US008951574B2

(12) United States Patent
Gehri et al.

(10) Patent No.: US 8,951,574 B2
(45) Date of Patent: Feb. 10, 2015

(54) STERILISATION AND CONSERVATION OF LIQUIDS

(75) Inventors: Martin Christian Adrian Gehri, Grossaffoltern (CH); Bernhard Keller, Meikirch (CH); Peter Regenass, Lagenthal (CH)

(73) Assignees: Bucher AG Langenthal, Langenthal (CH); Preentec AG, Fribourg (CH)

( * ) Notice: Subject to any disclaimer, the term of this patent is extended or adjusted under 35 U.S.C. 154(b) by 646 days.

(21) Appl. No.: 12/517,341

(22) PCT Filed: Dec. 20, 2007

(86) PCT No.: PCT/CH2007/000646
§ 371 (c)(1),
(2), (4) Date: Aug. 27, 2009

(87) PCT Pub. No.: WO2008/077265
PCT Pub. Date: Jul. 3, 2008

(65) Prior Publication Data
US 2010/0203161 A1 Aug. 12, 2010

(30) Foreign Application Priority Data

Dec. 22, 2006 (EP) .................................. 06405542

(51) Int. Cl.
*A01N 59/16* (2006.01)
*C02F 1/00* (2006.01)
(Continued)

(52) U.S. Cl.
CPC ................ *C02F 1/004* (2013.01); *A01N 25/10* (2013.01); *A01N 59/16* (2013.01); *C02F 1/688* (2013.01);
(Continued)

(58) Field of Classification Search
USPC .......................................................... 424/618
See application file for complete search history.

(56) References Cited

U.S. PATENT DOCUMENTS 2,595,290 A 5/1952 Quinn
4,198,296 A 4/1980 Doumas et al.
(Continued)

FOREIGN PATENT DOCUMENTS

EP 0 253 132 A1 1/1988
EP 0 727 427 A1 8/1996
(Continued)

OTHER PUBLICATIONS

V. Thomas, Murali Mohan Yallapu, B. Sreedhar, and S.K. Bajpai, "A versatile strategy to fabricate hydrogel—silver nanocomposites and investigation of their antimicrobial activity", Journal of Colloid and Interface Science 315 (2007) 389-395.*
(Continued)

*Primary Examiner* — Abigail Fisher
*Assistant Examiner* — Daniel L Branson
(74) *Attorney, Agent, or Firm* — Birch, Stewart, Kolasch & Birch, LLP.

(57) ABSTRACT

The invention relates to products, containing a solid biocide and a composite material (11) for the absorption of contaminants and the release of active ingredients as a composite preparation for the simultaneous, separate or programmed sequential application on sterilization and long-term conservation of a liquid (6) for purification. According to the invention, the activity of the solid biocide can be maintained by additionally treating the liquid (6) with the composite material (11), which absorbs (5.1, 5.2) from which the liquid and/or contaminants simultaneously releases active ingredients (13.1, 13.2) for sterilizing and/or reducing the contaminants (5.1, 5.2) in the liquid (6). The products and the method are particularly suitable for sterilizing and long-term conservation of water/oil emulsions which are contaminated by sulphur-containing compounds.

15 Claims, 2 Drawing Sheets

Figure 1:
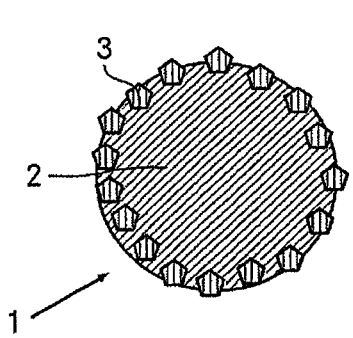

(51) Int. Cl.
*A01N 25/10* (2006.01)
*C02F 1/68* (2006.01)
*C10M 175/00* (2006.01)
*C10M 175/04* (2006.01)
*C02F 1/50* (2006.01)

(52) U.S. Cl.
CPC ... *C10M 175/0016* (2013.01); *C10M 175/0091* (2013.01); *C10M 175/04* (2013.01); *C02F 1/50* (2013.01); *C02F 2303/04* (2013.01); *C10N 2230/16* (2013.01); *C10N 2240/40* (2013.01); *Y10S 210/902* (2013.01)
USPC .......................................... 424/618; 210/902

(56) References Cited

U.S. PATENT DOCUMENTS

| | | | |
|---|---|---|---|
| 5,064,534 A | | 11/1991 | Busch et al. |
| 5,792,793 A | * | 8/1998 | Oda et al. ...................... 514/495 |
| 6,838,095 B2 | * | 1/2005 | Newman et al. ............. 424/618 |
| 2003/0140785 A1 | | 7/2003 | Koslow |
| 2004/0188338 A1 | * | 9/2004 | Kato et al. .................... 210/283 |
| 2005/0013788 A1 | * | 1/2005 | Held et al. ................. 424/70.16 |

FOREIGN PATENT DOCUMENTS

| | | |
|---|---|---|
| EP | 1 462 416 A2 | 9/2004 |
| JP | 2000-302617 A | 10/2000 |
| JP | 2004-290874 A | 10/2004 |
| WO | WO-03/064330 A1 | 8/2003 |

OTHER PUBLICATIONS

Sibel Duran, Dilek Solpan, and Olgun Guven, "Synthesis and characterization of acrylamide±acrylic acid hydrogels and adsorption of some textile dyes", Nuclear Instruments and Methods in Physics Research B 151 (1999) 196±199.*
Y. Murali Mohan, Kyungjae Lee, Thathan Premkumar, and Kurt E. Geckeler, "Hydrogel networks as nanoreactors: A novel approach to silver nanoparticles for antibacterial applications", Polymer 48 (2007) 158e164.*
A. Pourjavadi, M. S. Amini-Fazl, and H. Hosseinzadeh, "Partially Hydrolyzed Crosslinked Alginate-graft-Polymethacrylamide as a Novel Biopolymer-Based Superabsorbent Hydrogel Having pH-Responsive Properties", Macromolecular Research, vol. 13, No. 1, pp. 45-53 (2005).*
Hu et al., "Copper/activated carbon as catalyst for organic wastewater treatment", Carbon (1999), vol. 37, Issue 4, pp. 631-637.*
Notice of Reasons for Rejection dated Apr. 3, 2012 for Application No. 2009-541730.

* cited by examiner

STERILISATION AND CONSERVATION OF LIQUIDS

TECHNICAL FIELD

The invention relates to products and to a process for the sterilization and long-term preservation of a fluid to be purified.

PRIOR ART

Fluids, such as water, fuels, cooling liquids, lubricants, engine oils, but also physiological liquids are subjected to a very wide variety of microorganisms depending on environmental influences. To maintain the desired fluid function, in particular those fluids which are used for a long time (e.g. cooling liquids or lubricant oils in technical apparatuses) have to be protected from bacterial and fungal attack by adding sterilizing agents and/or preservatives.

When using liquid sterilizing agents or preservatives, although attack by microorganisms is prevented, at the same time, however, the desired properties of the fluids may also be adversely affected. In the case of the provision of bathing water or drinking water, for example, added to this is the fact that only toxicologically acceptable biocides can be used as sterilizing agents or preservatives since living things come into direct contact with the fluid or even consume it.

However, if biocides are used in solid form, the problems given above are circumvented. The biocides can be retained in a fluid tank in a simple manner, e.g. by filtration, or are directly integrated into a filter system.

US 2003/0140785 describes a filter medium with an antibacterial effect, comprising a polymer active granulate which is incorporated into a carrier. The active particles have a diameter of 0.1-5000 μm (micrometers). The active ingredient used is either metallic or complex-bonded silver. The silver is not released into the surroundings upon use and therefore has a catalytic effect. The polymer comprises a crosslinked polyacrylamide and a sorbent anchored therein. The filter medium is suitable for the sterilization of liquids, in particular also for the sterilization of water or industrial liquids.

U.S. Pat. No. 5,792,793 describes an antibacterial active ingredient which can be used on a large number of carriers. The biocidal effect of the active ingredient arises due to silver ions bonded in thiol complexes. Suitable carriers are solid particles or liquids. The materials used for solid carriers here are various polymers and synthetic resins, in particular acrylic synthetic resins. The particles have a diameter between 10 μm (micrometers) and 10 mm. The silver remains bonded in the complexes, the complexes being anchored on the carrier. The antibacterial active ingredient bonded to a carrier can be used in tanks and for water preparation, but also in medicinal areas. The carrier particles here can be freely introduced into the tank with the liquid to be treated.

However, it has been found that, depending on the composition of the fluid, the biocidal properties of surface-active solid biocides considerably diminish or are even suppressed completely despite a catalytic action mechanism even after a short time. In order to maintain a sterilizing and preserving effect, additional biocide must therefore be added to the fluid. However, this process has an impact on the environment and is expensive since a large amount of preservative is used unnecessarily, which loses its effect after a short time.

There is therefore still a need for a process for the sterilization and long-term preservation of a fluid and for corresponding sterilizing agents and preservatives which do not have the disadvantages mentioned above.

DESCRIPTION OF THE INVENTION

It is an object of the invention to provide products associated with the technical field specified at the start and also a corresponding process which permit a sterilization and long-term preservation of a fluid that is toxicologically acceptable in terms of the environment and moreover minimize the consumption of sterilizing agent and preservative.

The attainment of the object is defined by the features of the claims. According to the invention, for the sterilization and preservation of fluids, products are used as combination preparation which is based on a combination of a solid biocide and a composite material for the absorption of contaminants and release of active ingredients. In this connection, to improve the durability of the solid biocide, the fluid to be purified is additionally treated with the composite material, which absorbs contaminants from the solution and at the same time releases active ingredients for the sterilization and/or reduction of the contaminants in the fluid. The combination preparations according to the invention are used here simultaneously, separately or staggered in the fluid to be purified.

Compared with the prior art, the products according to the invention and the present process offer several advantages. For example, by removing contaminants from the fluid with the composite material, it is ensured that the solid biocide is not contaminated by contaminants, thereby neutralizing its biocidal activity.

Since the sterilizing agents and/or preservatives used are solids, these can be filtered off easily. During the sterilization and preservation of fluids which are used in a fluid cycle (e.g. in a coolant cycle; in a lubricant cycle or in the processing of drinking water and bathing water), it is advantageous if the sterilizing agents and/or preservatives are present e.g. only in one equalizing vessel or one tank. This means, on the one hand, that people who come into contact with the fluid do not come into contact with the biocidal and, if need be, toxic substances for the sterilization and preservation. On the other hand, it is ensured that the actual function of the fluid, i.e. the lubrication of a machine, is not adversely affected by sterilizing agent or preservatives dissolved, emulsified or suspended therein.

Through the process according to the invention, a best possible toxicological unburdening of the environment is achieved since the required amounts of sterilizing agent and/or preservative are minimized.

Preferably, the solid biocide used in the products is one substance or a substance mixture which, upon contact, in particular upon surface contact, with microorganisms, produces a germicidal killing effect on the microorganisms on account of a catalytic mechanism. This ensures a long-lasting effect of the solid biocide since it is not consumed during use. In particular upon contact of the solid biocide with bacteria and, or fungi, a bactericidal and/or fungicidal effect arises. This can be brought about, for example, by an oligodynamic effect which is based on the harmful effect of metal cations on living cells. In particular, cations of e.g. Hg, Ag, Cu, Sn, Fe or Pb exhibit this effect. Especially in the case of engine oils, lubricants, cooling emulsions or in the medical sector, it is important to thoroughly prevent the bacterial and fungal attack which often arises.

Alternatively, a solid biocide can also be used which removes the microorganisms from the fluid by absorption and kills them inside the biocide through the release of active ingredients. This action mechanism has the advantage that the fluid is protected against inactive biomaterial.

Upon adding the composite material to the fluid, at least some of the active ingredients present in the composite material are released into the fluid and at the same time contaminants are absorbed from the fluid in the region of the surface or in the inside of the composite material. This double function of the composite material leads to an efficient elimination of contaminants from the fluid. Thus, contaminants which e.g. on account of their size or chemical structure cannot be absorbed within a composite material can be precipitated out in the fluid by the released active ingredients or be converted to an inert form by a chemical reaction.

At the same time, the release of sterilizing active ingredients into the fluid causes all microorganisms to be killed in a rapid sterilization step for fluids heavily attacked by microorganisms. The microorganisms newly arriving in the fluid can then be eliminated without problems by a small amount of preferably catalytic solid biocide.

The products according to the invention and the processes according to the invention are suitable in particular for fluids which contain contaminants which reduce the effect of the surface-active solid biocides. The fluids themselves can, for example, be in the form of liquids or gases and consist of one pure substance or substance mixtures, which may be homogeneous or inhomogeneous. The process for the purification of emulsions which preferably comprise oil and water and in particular are used as cooling lubricant emulsion is particularly advantageous. Microorganisms, such as e.g. bacteria, which live in such emulsions find ideal conditions for multiplication and in most cases produce a plurality of different metabolic products in the fluid which can severely adversely affect the biocidal effect of the solid biocide by e.g. positioning themselves on the surface.

Microorganisms which occur in oily emulsions produce inter alia a large number of sulfur-containing compounds, which mostly smell bad and have a high affinity or reactivity to/with a large number of substances, so as, for example, metals. The composite material for the absorption of contaminants and release of active ingredients is therefore advantageously configured so that it absorbs and/or precipitates out sulfur and/or organic and/or inorganic sulfur compounds which are present as contaminants in the fluid and, or converts them chemically into an inert form.

Depending on the fluid to be purified, the composite material, however, may also be configured such that it absorbs and neutralizes other contaminants, e.g. oxygen-containing or metal-containing compounds.

It is furthermore advantageous if the active ingredients released from the composite material lead to the precipitation of the contaminants in the form of solids and if the released active ingredients moreover have an antibiotic effect, which is in particular a bactericidal and/or fungicidal effect. The precipitation of the contaminants permits simple filtration of the undesired substances, as a result of which the function of the fluid is retained and the toxicological impact on the environment is reduced since the precipitated waste products e.g. no longer take part in the fluid cycle. Particularly in the case of engine oils, lubricants, cooling emulsions, liquids in the sanitary sector or in the medicinal sector, it is indispensable to thoroughly prevent the bacterial and fungal attack which often occurs since microorganisms of this type, e.g. through the release of acid, greatly alter the properties of the fluids used or as in the sanitary or in the medical sector even become a direct risk for people.

The released active ingredients of the composite material are particularly advantageously metals and, or metal compounds, which are preferably Ag and in particular Cu and Zn. Metals and metal compounds have a high affinity toward a large number of in particular oxygen-containing and sulfur-containing compounds. Upon a release into a fluid to be purified, the contaminants can thus be bonded and neutralized by the metals or metal compounds or be converted into an inert form by a chemical reaction. Moreover, many metals, in particular Ag, but also Cu or Zn, have a biocidal effect which, upon releasing to the fluid, leads to a killing of the microorganisms present. In particular, it is known that Ag ions are able to influence the permeability of cell walls and to bond sulfur bridges in proteins, which nay lead to a disturbance of the enzyme functions in the cell and ultimately to the death of the microorganisms.

Upon adding the solid biocide to the fluid, preferably no chemical compounds, in particular no metals or metal compounds, are released into the fluid. Specifically, this is understood as meaning that the amount of released chemical compounds in the thermodynamic equilibrium per 9.8 g of solid biocide is less than 2 µg/l. The solid biocide acts then only on account of surface interactions with the microorganisms. This catalytic action mechanism means that no chemical substances are consumed for developing the biocidal effect. The solid biocides can accordingly remain for a long time in the fluid without their activity decreasing, which minimizes the consumption of resources and reduces the toxicological impact on the environment.

With regard to the absorbing and active ingredient-releasing composite material, the object according to the invention is achieved in that it comprises a substrate and metals or metal compounds incorporated and/or bonded therein.

Metals include here on the one hand metal atoms, which may be present as cations, anions or in neutral form. On the other hand, the metals can, however, also be present as purely metallic composites, consisting e.g. of a plurality of metal atoms. Metal compounds can be, for example, metal complexes or metal-containing solids, such as e.g. metal oxides, metal salts or metal-containing zeolites. The metal-containing substances here may be present in atomic or molecular form, as amorphous or crystalline particles with dimensions in particular in the nanometer range and/or as macroscopic solids, in particular with a size in the micrometer range.

Preferably Ag and particularly preferably additionally Zn and/or Cu are present as metal or in the metal compounds of the absorbing and active ingredient-releasing composite materials. Metals of this type and compounds thereof have a high affinity towards a large number of in particular oxygen-containing and sulfur-containing compounds, whereby an absorption effect for contaminations of this type is achieved by the composite material. The metals present moreover have a biocidal effect which, when added to the fluid, leads to a killing of the microorganisms present. The germicidal effect is based inter alia on the oligodynamic effect, which brings about a change in the osmotic pressure within the microorganism. Moreover, in particular Ag ions can form hydroxyl radicals via a catalytic mechanism; in the fluid, these likewise have a damaging effect on microorganisms.

Through the use of a substrate, it is possible to intercalate different metals or other active ingredients in the substrate without developing the composite material again each time. The metals or metal compounds can, for example, be intercalated into the substrate by weak interactions, such as e.g. van-der-Waals interactions or electrostatic interactions. In another variant, the metals or metal compounds can be bonded to the substrate by chemical bonds, such as e.g. covalent bonds or complexation.

In principle, suitable substrate materials are inorganic or organic compounds which can be converted by a suitable treatment into porous solids of defined form and size and are chemically inert as far as possible. In one advantageous embodiment, the substrates comprise modified polysaccharides and particularly preferably additionally polyacrylamides and/or amines. Substrates of this type are chemically inert in many fluids, in particular in water/oil emulsions.

In one further variant, substrates can be used which have a precisely defined pore size and chemical composition. For example, zeolites are suitable. As a result, it is possible to absorb contaminants of a certain size or having certain chemical properties from the fluid in a targeted manner. A chemical selectivity is thus achieved which prevents the composite materials unnecessarily absorbing contaminants which do not contaminate the solid biocides at all. Consequently, the consumption of required chemical substances can additionally be reduced.

With regard to the solid biocide, the object is achieved according to the invention in that it is advantageously surface-active and comprises a substrate and metal or metal compounds which are arranged in or on and/or bonded to the surface of the substrate and/or close to the surface.

As in the case of the composite material, the metals here include on the one hand metal atoms, which may be present as cations, anions or in neutral form. On the other hand, the metals, however, may also be present as purely metallic composites, consisting e.g. of a plurality of metal atoms. Metal compounds can be, for example, metal complexes or metal-containing solids, such as metal oxides, metal salts or metal-containing zeolites. The metal-containing substances here may be in atomic or molecular form, as amorphous or crystalline particles with dimensions, in particular in the nanometer range, and/or as macroscopic solids, in particular having a size in the micrometer range.

As a result of the concentration in the region of the surface of the substrate, the amount of metals or metal compounds can be significantly reduced compared to a homogeneous distribution within the entire substrate.

It is also possible to attach the active ingredients close to the surface, but not directly on the surface of the substrate. If, moreover, a substrate with a porous structure is used, it can be controlled e.g. via the pore size which microorganisms can, on account of their size, pass through the pores sufficiently close to the active ingredients. Consequently, it is e.g. possible to use surface-active solid biocides which are able to selectively kill certain microorganisms.

In principle, suitable substrate materials for the solid biocides are inorganic or organic compounds which can be converted by a suitable treatment into solids of defined form and size and are chemically inert as far as possible. In one advantageous embodiment, the substrates comprise alginates and preferably additionally polyacrylamides and/or amines and/or aluminum silicates or zeolites. Alginates, or salts of alginic acid, are polymers of α-L-guluronic acid and β-D-mannuronic acid, which are very highly suitable for gel formation and are physiologically acceptable.

In the solid biocides, Ag is preferably present as metal or in the metal compounds, which in particular is present in an Ag complex, particularly preferably in an Ag amino complex. Ag and its compounds have a strongly biocidal effect on a very wide variety of microorganisms. In particular Ag in ionic form has a greatly damaging effect on living cells due to the oligodynamic effect, as described above for the composite materials.

The substrates of the solid biocide and/or of the composite material are advantageously configured as hydrogels which are preferably swellable and/or elastic. Hydrogels are water-containing polymers, but are themselves not soluble in water. The molecules and polymers in the hydrogel are bonded e.g. by covalent or ionic bonds and/or by looping of the polymer chains and form a three-dimensional porous network. On account of hydrophilic polymer components, hydrogels can physically swell in water without, however, being dissolved. The fact that hydrogels have high biocompatibility is particularly advantageous for applications of the process according to the invention in the medical sector. At the same time, hydrogels also have high mechanical load-bearing capacity and chemical stability, meaning that they can be used without problems in strongly flowing and chemically aggressive fluids, such as e.g. in lubricant emulsions, engine oils, cooling emulsions or corresponding fluid cycles. A high chemical stability is of great advantage particularly for the solid biocides since the solid biocides remain in the fluid to be purified over a long period and are attacked by various chemical substances.

Moreover, the ability to swell has a positive effect on the absorbing properties of the composite material. As a result of the increase in volume upon swelling, openings and channels are formed in the hydrogel, as a result of which the contaminants can rapidly diffuse from the fluid into the inner areas of the composite material. This leads to a high absorption capacity, which means that the contaminants are removed from the fluid within a short period. At the same time, the swelling permits a rapid release of the active ingredients from the hydrogel into the fluid to be purified. Both effects result in the best possible protection of the solid biocides by the contaminants being rapidly absorbed and microorganisms present being killed by the released active ingredients within a short period.

The solid biocide and/or the composite material are preferably present in the form of polyhedra, such as cuboids or plates, spherical particles, as granulate, as powder grains or as coatings on carrier materials, in particular on vessel walls. The form of the materials can be adapted depending on the intended use. Particular preference is given to the coating of vessel walls. Thus e.g. the purely surface-active solid biocide, which has a long-term effect, can be applied as a coating to one wall of a fluid reservoir and the absorbing and active ingredient-releasing composite material is added as granulate. Consequently, the composite material, after developing its effect, can be removed again from the fluid.

If the solid biocides and/or the composite materials are in the form of spherical particles or individual grains of a granulate, these preferably have a diameter of 0.1-5 mm, in particular of 0.5-1.2 mm. The surface of the materials is thereby optimized relative to the volume. With the surface-active solid biocides, it is thus ensured that a sufficiently large surface is available for interaction with the microorganisms per mass of added material. For the absorbing composite materials, it is simultaneously ensured that sufficient absorption volume for the contaminants is available.

The solid biocides and composite materials can in principle be added simultaneously to the fluid to be purified. This has the advantage that a fluid can be very easily sterilized and preserved in the long-term through a single addition of the products. In order, however, to achieve the optimum effect of the products, it is advantageous to treat the fluid to be purified in a first process step only with the composite material for absorption and release of active ingredients, end only in a second process step to add surface-active solid biocides. All contaminants and microorganisms are thereby firstly removed from the fluid and the solid biocide added subsequently can develop its full effect. If at a later time a large number of microorganisms or contaminants passes into a fluid already admixed with the solid biocide, then naturally again absorbing and active ingredient-releasing composite material can be added in order to rapidly reduce the number of microorganisms and the contaminants and thus to maintain the biocidal effect of the solid biocide.

Further advantageous embodiments and feature combinations of the invention arise from the detailed description below and the entirety of the patent claims.

SHORT DESCRIPTION OF THE DRAWINGS

The drawings used to illustrate working examples show diagrammatically:

FIG. 1 the structure of a surface-active solid biocide.

Figure 2:
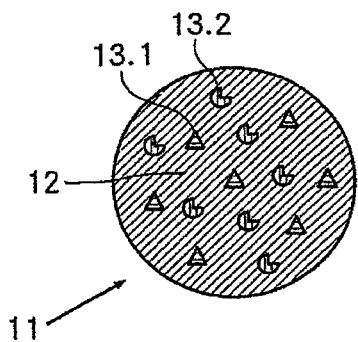

FIG. 2 the structure of a composite material for the absorption and release of active ingredients.

Figure 3:
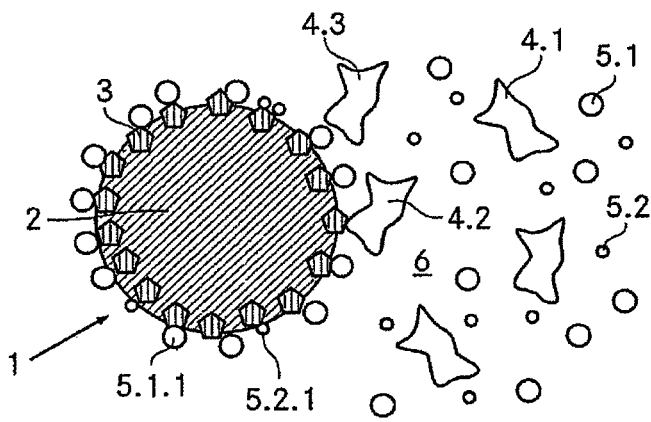

FIG. 3 the addition of solid biocide to a fluid contaminated with contaminants.

Figure 4:
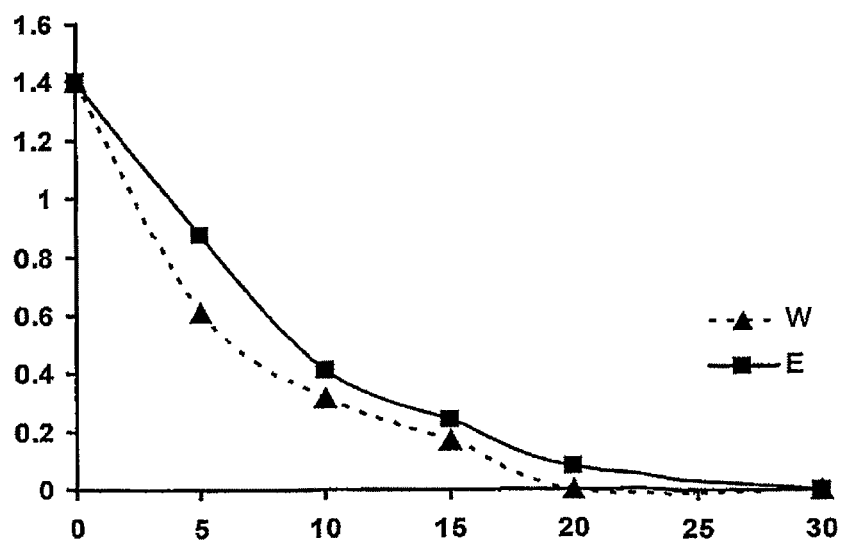

FIG. 4 the decrease over time of the sulfur concentration in an aqueous solution and an emulsion following the addition of composite material.

Figure 5:
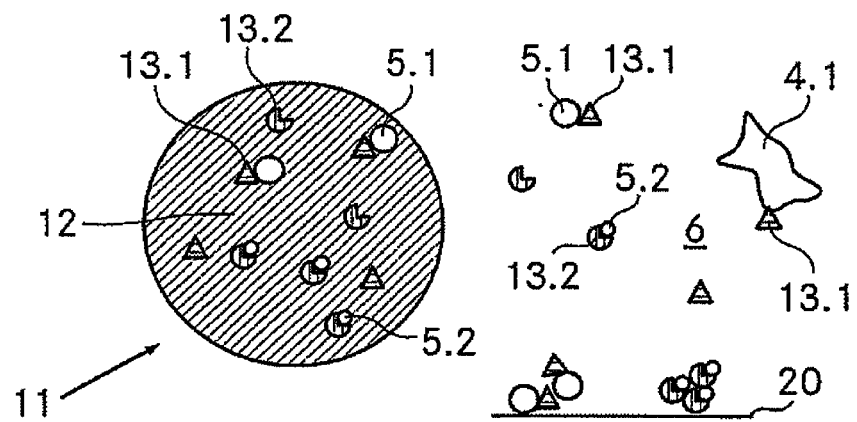

FIG. 5 the mode of action of an absorbing and active ingredient-releasing composite material.

Figure 6:
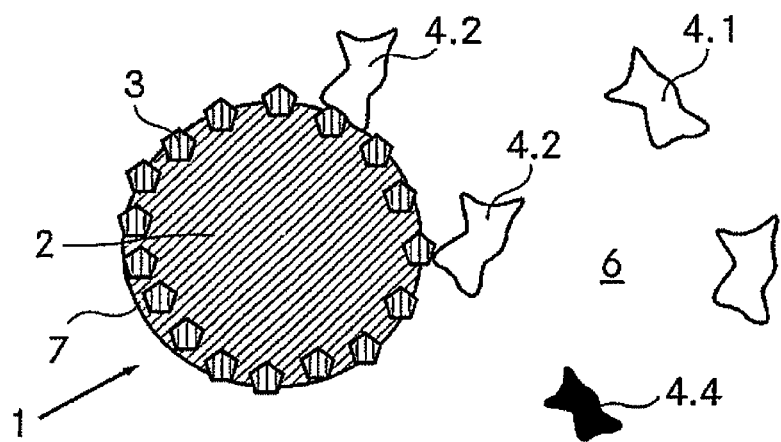

FIG. 6 the mode of action of a solid biocide following elimination of the contaminants in the fluid.

In principle, the same parts are provided with the same reference numbers below.

WAYS TO CARRY OUT THE INVENTION

A solid biocide 1 consists, as shown in FIG. 1, of a substrate 2 made of the organic components sodium alginate, acrylamide, N,N'-methylenebisacrylamide and if appropriate aluminum silicates. As surface-active substances 3, Ag amino complexes are introduced into areas of the substrate 2 close to the surface.

FIG. 2 shows the structure of an absorbing and active ingredient-releasing composite material 11. The substrate 12 consists of aqueous modified polysaccharides, acrylamide and N,N'-methylenebisacrylamide. The active ingredients 13.1 are incorporated therein in the form of Ag amino complexes. As additional active ingredient 13.2, Zn is incorporated in metallic form.

FIG. 3 shows contaminants 5.1, 5.2 dissolved in a fluid 6 which consist primarily of various sulfur-containing compounds. They have a high affinity to the surface-active substances 3 and/or the Ag amino complexes of the solid biocide 1. Consequently, the surface-active substances 3 are contaminated by the adsorbed contaminants 5.1.1, 5.2.1 and lose their biocidal function. To sterilize the fluid 6, however, it is imperative that the bacteria 4.1 come into close contact with the surface-active substances 3 of the solid biocide 1, as shown for a bacterium 4.2. Bacteria 4.3 which contact the solid biocide at a point which is already occupied by absorbed contaminants 5.1.1, 5.1.2 are not killed. Since only a small amount of uncontaminated surface-active substances 3 is still available, too many microorganisms 4.1 remain in the fluid, as a result of which their number further increases through rapid multiplication.

FIG. 4 shows the course of the $S^{2-}$ concentration units of ppm ("parts per million", vertical axis) in the aqueous solution W (triangular data points) and of the emulsion E (quadratic data points) as a function of the time t in minutes (horizontal axis). Here, it can be seen that the initial $S^{2-}$ concentration in both liquids at time t=0 min is 1.4 ppm and just after t=5 min has dropped to less than 0.9 ppm in the emulsion E and 0.6 ppm in the aqueous solution W. The $S^{2-}$ concentration at time t=10 min is 0.4 ppm in the emulsion E and 0.3 ppm in the aqueous solution W. After t=15 min, still ca. 0.2 ppm of $S^{2-}$ are present in both liquids. After t=20 min, already no more $S^{2-}$ is detectable in the aqueous solution W, whereas in the emulsion E less than ca. 0.1 ppm are present. After 30 min, both solutions are completely free of $S^{2-}$, i.e. the concentrations in each case are 0 ppm.

FIG. 5 shows the processes in a fluid in diagram form. If the composite material 11 is added to the fluid, the Ag-containing active ingredients 13.1 are partially released to the fluid 6. Within the fluid 6, the active ingredients 13.1 react with the contaminants 5.1, as a result of which these are converted to an inert form or precipitated out and position themselves on vessel walls 20 as solid bodies. At the same time, the microorganisms 4.1 are killed by the active ingredients 13.1. Moreover, the composite material 11 absorbs some of the contaminants 5.1 present in the fluid 6 by binding them to the still incorporated active ingredients 13.1.

FIG. 6 shows diagrammatically the mechanism of action of the solid biocide 1 on microorganisms 4.1 dissolved in the fluid 6. Microorganisms 4.2 which have contact with the solid biocide 1 are killed by the catalytic and biocidal effect of the surface-active substances 3. They then pass back again into the fluid 6 and are in the form of inactive biomaterial 4.4. On account of the fact that as a result of the pretreatment of the fluid with composite material 11, contaminants are virtually no longer present, the surface 7 of the solid biocide 1 remains clean, thus permitting a long-term biocidal effect and/or a preservation of the fluid.

Solid Biocide

Example A

Aqueous sodium alginate (12 ml, 4% w/v, with low viscosity, Sigma), water (5 ml), aqueous acrylamide (8 ml, 40% in $H_2O$, purum, Fluka), aqueous N,N'-methylenebisacrylamide (4 ml, 2% w/v) and N,N,N',N'-tetramethylethylenediamine (0.1 ml in 1 ml of $H_2O$) were mixed together to give a solution. Spherical droplets with a diameter between 0.1-1.2 mm were formed from the solution using an encapsulation system (Nisco Engineering) with a die opening of 0.08-0.6 mm. The spherical droplets were added to a stirred solution of ammonium peroxodisulfate (80 ml, 1% w/v, with 0.1 M calcium chloride) at 60° C. in a beaker and incubated for 30 min, during which spherical particles are formed. The particles were separated from the hardening solution by sieving, washed 5 times with 100 ml of water, ripened in an aqueous solution of sodium citrate (100 ml, 0.1 M) for 6 hours at room temperature (RT) and then washed again 5 times with 100 ml of water. The citrate treatment and the washing operations were repeated twice. The resulting spherical particles were boiled in an aqueous solution of potassium hydroxide (500 ml, 5% w/v) for 5 hours. In parallel to this, a 3-10% strength solution of Ag amino complexes with $AgNO_3$ and 2-methylaminopyridine was prepared, and 50 ml of this were added to the aqueous solution with the spherical particles while boiling at various temperatures. After boiling and simultaneous removal of ammonia for 4-12 hours, the spherical droplets were separated off by sieving, incubated three times in 5 liters of water for 2 hours in each case and finally dried at elevated temperatures and in vacuo. The weight of the dried spherical particles of poly(acrylamide-co-potassium acrylate-co-N,N'- methylenebisacrylamide) is 7.8±0.5 mg and 203±10 mg after contact for 3 hours with 10 ml of distilled water at room temperature.

Solid Biocide

Example B

Aqueous sodium alginate (12 ml, 4% w/v, low viscosity, Sigma), water (5 ml), aqueous acrylamide (8 ml, 40% in $H_2O$, purum, Fluka), aqueous N,N'-methylenebisacrylamide (4 ml, 2% w/v) and N,N,N',N'-tetramethylethylenediamine (0.1 ml in 1 ml of $H_2O$) were mixed together to give a solution. 0.5 g of aluminum silicate in the form of a fine powder were added to this and stirred for 2.5 hours. Spherical droplets with a diameter between 0.1-1.2 mm were formed from the solution using an encapsulation system (Nisco Engineering) with a die opening of 0.08-0.6 mm. The spherical droplets were added to a stirred solution of ammonium peroxodisulfate (80 ml, 1% w/v, with 0.1 M calcium chloride) at 60° C. in a beaker and incubated for 30 min, during which spherical particles were formed. The particles were separated from the hardening solution by sieving, washed 5 times with 100 ml of water, ripened in an aqueous solution of sodium citrate (100 ml, 0.1 M) for 6 hours at room temperature (RT) and then washed again 5 times with 100 ml of water. The citrate treatment and the washing operations were repeated twice. The resulting spherical particles were boiled in a 5% strength aqueous solution of $AgNO_3$, incubated for 45 min, washed 3 times with 5 liters of milliQ water for 2 hours in each case and stored at 5° C. in water.

Composite Material

Example C

Ag amino complexes were synthesized by stoichiometric mixing of $AgNO_3$ and aminopyridines. Subsequently, 80 ml of a 3% strength aqueous solution of modified polysaccharides were mixed at 60° C. with 20 ml of an aqueous solution of 1-15 g of the Ag amino complexes and heated for 30 min.

Spherical droplets with a diameter between 0.1-1.2 mm were formed from the solution using an encapsulation system (Nisco Engineering) with a die opening of 0.08-0.6 mm. The spherical droplets were added to liquid nitrogen in a beaker and stirred for 5 min. During this, spherical particles are formed, which were separated off from the solution by sieving.

Composite Material

Example D

Water (5 ml), aqueous acrylamide (8 ml, 40% w/v, purism, Fluka), aqueous N,N'-methylenebisacrylamide (4 ml, 2% w/v) and N,N,N',N'-tetramethylethylenediamine (0.1 ml in 1 ml of $H_2O$) and aqueous modified polysaccharides (20 ml, 5% w/v) were mixed together to give a solution and heated at 50° C. for 30 min. 1.3 g of fine Zn powder and 0.7 g of $AgNO_3$ were then added. Spherical droplets with a diameter between 0.1-1.2 mm were formed from the solution using an encapsulator system (Nisco Engineering) with a die opening of 0.08-0.6 mm. The spherical droplets were added to a stirred solution of ammonium peroxodisulfate (80 ml, 1% w/v, with 0.1 M calcium chloride) at 60° C. in a beaker and incubated for 30 min, during which spherical particles were formed.

Comparative Experiment

Example E

In a first experiment, for comparison purposes, various types of soiled, commercially available MOTOREX cooling lubricant emulsions based on water/oil were treated with purely surface-active solid biocides 1 according to the process known from the prior art and their biocidal effect was investigated as a function of time. For this, the number of bacteria per milliliter of emulsion at different time points following the addition of the solid biocides 1 was determined. For better mixing, the emulsions were in each case stirred or shaken following the addition of the solid biocides 1. To determine the number of bacteria, in each case three Petri dishes were coated with identical and defined aliquots and/or part samples of the emulsion and incubated for 24 hours. The number of bacteria was then determined automatically using an Acolyte™ colony counter on all three incubated part samples.

Table 1 gives a summary of the experiments. In a first experiment (No. 1), the number of bacteria 4.1 per ml of a heavily soiled emulsion prior to treatment with the solid biocide 1 is greater than $10 \cdot 10^7$. After adding 39 mg of solid biocide 1 per 50 ml of emulsion and an incubation time of 72 h, the bacteria number has dropped to $10 \cdot 10^2$ bacteria/ml. After an incubation time of 126 h, without further addition of solid biocide 1, the number of bacteria 4.1 has already increased again to $10 \cdot 10^4$ bacteria/ml. In the second experiment (No. 2) with an emulsion of the same type, the number of bacteria 4.1 prior to the treatment with the solid biocide 1 after storage for 145 h at room temperature is $10 \cdot 10^6$. After adding 156 mg of solid biocide 1 per 45 ml of emulsion and an incubation time of 48 h, the number of bacteria drops to $10 \cdot 10^4$ per ml of emulsion. The number of bacteria/ml after an incubation time of 196 h, however, is already again $10 \cdot 10^6$ and no longer changes even after an incubation time of 300 h.

TABLE 1

| Experiment No. | Type of emulsion | Addition of solid biocide | Incubation time | Bacteria/ml |
|---|---|---|---|---|
| 1 | 7788 (090206) | 0 | 0 | >$10 \cdot 10^7$ |
|  |  | ca. 39 mg/50 ml | 72 h | $10 \cdot 10^2$ |
|  |  |  | 126 h | $10 \cdot 10^4$ |
| 2 | 7788 (240206) | 0 | 145 h | $10 \cdot 10^6$ |
|  |  | ca. 156 mg/45 ml | 48 h | $10 \cdot 10^4$ |
|  |  |  | 196 h | $10 \cdot 10^6$ |
|  |  |  | 300 h | $10 \cdot 10^6$ |

The two experiments clearly show that the emulsions used cannot be long-term sterilized and preserved using purely surface-active solid biocides 1. This is attributed to the contamination of the solid biocides 1 with contaminants 5.1.1, 5.2.1 from the emulsions. On account of the yellowish and/or brownish discoloration of the solid biocides 1 during the experiments, it can be concluded that the contaminants 5.1.1, 5.2.1 are at least partially sulfur-containing compounds. Sulfur-containing substances are caused inter alia by metabolic products of the bacteria or fungi 4.1 in the emulsion and are particularly problematic since they have a high affinity to the Ag-containing solid biocides 1 used.

Desulfurization

Example F

The composite materials for the absorption and active ingredient release 11 were investigated in a first test with regard to their sulfur reduction ability. To measure the sulfur reduction of sulfur-containing liquids, the following experiments were carried out:

500 ml of water (bidistilled) were admixed with 1.4 ppm of sulfur ($S^{2-}$) and treated with stirring with in each case 1 g of composite material 11 (example C) which was cast in the form of plates. For the "desulfurization", an aqueous stock solution with a concentration of 14 ppm of $S^{2-}$, starting from sodium sulfide, was used here.

The sulfur concentrations were determined in each case after 0, 5, 10, 15, 20, 25 and 30 min by spectroscopy via specific color detections. The same experiment was carried out with 500 ml of an emulsion (Motorex 7788) instead of water.

Composite materials for the absorption and active ingredient release 11 were then used for the sterilization of various types of soiled, commercially available MOTOREX cooling lubricant emulsions 6 based on water/oil. Prior to the treatment, all of the emulsions 6 used had a high bacteria concentration, which is at least $10 \cdot 10^6$ bacteria/ml. Emulsions of the same type were here in part soiled to varying degrees since they had different histories. For the sterilization and removal of the contaminants 5.1, 5.2, in each case 100 mg of the composite material 11 (example D) were added to the emulsions 6 per ml of the emulsion and the number of bacteria 4.1 was determined at various times according to the process described above. Table 2 gives an overview of the experiments carried out and results. It can clearly be seen that for the majority of the emulsions 6, bacteria 4.1 can no longer be detected even after an incubation time of 24 h. After 6 days (6 d), only one emulsion (7711) 6 still has a small amount of bacteria 4.1 and after 20 days (20 d), all of the emulsions 6 are free from bacteria 4.1. The results clearly demonstrate the biocidal effect of the composite materials 11.

TABLE 2

| Experiment No. | Type of emulsion | Bacteria/ml after 24 h | Bacteria/ml after 6 d | Bacteria/ml after 20 d |
| --- | --- | --- | --- | --- |
| 1 | 7788 | 0 | 0 | 0 |
| 2 | 7788 | 0 | 0 | 0 |
| 3 | 7788 | $10 \cdot 10^3$ | 0 | 0 |
| 4 | 7788 | 0 | 0 | 0 |
| 5 | 7755 Aero | 0 | 0 | 0 |
| 6 | 7755 Aero | $10 \cdot 10^2$ | 0 | 0 |
| 7 | 7755 Aero | 0 | 0 | 0 |
| 8 | 7733 | 0 | 0 | 0 |
| 9 | 7733 | $10 \cdot 10^2$ | 0 | 0 |
| 10 | 7722 | 0 | 0 | 0 |
| 11 | 7722 | 0 | 0 | 0 |
| 12 | 7722 | 0 | 0 | 0 |
| 13 | 7722 | 0 | 0 | 0 |
| 14 | 7711 | $10 \cdot 10^4$ | $10 \cdot 10^1$ | 0 |
| 15 | V 8.01 | 0 | 0 | 0 |

Preservation with Solid Biocide

Example H

The preservation effect of the solid biocides 1 was investigated by the following experiment: 1 liter of a sterile Motorex emulsion of the type 7788 purified of contaminants was inoculated with 100 µl of a bacteria-containing emulsion of the same type (7788) to $10 \cdot 10^3$ bacteria per ml and admixed with a spherical particle (mass=7.8 mg) of the solid biocide 1 (example A). The number of bacteria 4.1 was determined at various times in accordance with the process described above. Table 3 shows a summary of the experiments. The results clearly show that the solid biocide 1 is able to completely reduce a bacteria concentration of $10 \cdot 10^3$ bacteria/ml within 7 days and to preserve the emulsion for 19 days. After 19 days, the sterile emulsion was inoculated for the second time, but this time with 500 µl of the bacteria-containing emulsion of the type 7788, resulting in a bacteria concentration of $50 \cdot 10^3$ bacteria/ml. Two days after the second inoculation (t=21 days), the bacteria 4.1 have greatly multiplied and a concentration of $10 \cdot 10^6$ bacteria/ml is present, but this decreases after just a further 10 days to $10 \cdot 10^2$ bacteria/ml. The experiment clearly shows that an emulsion sterilized and purified by the composite material can be preserved in the long-term by a small amount of solid biocide 1. In this connection, the solid biocide 1 can also reduce again a concentration which has increased in the meantime of up to $50 \cdot 10^3$ bacteria/ml. Higher bacteria concentrations, however, lead to deactivation of the surface activity of the solid biocides 1, as described above.

TABLE 3

| t [Days] | Bacteria/ml | Remarks |
| --- | --- | --- |
| 0 | $10 \cdot 10^3$ | |
| 7 | 0 | |
| 10 | 0 | |
| 13 | 0 | |
| 19 | 0 | |
| 19 | $50 \cdot 10^3$ | Following addition of 500 µl of the bacteria-containing emulsion |
| 21 | $10 \cdot 10^6$ | |
| 25 | $10 \cdot 10^4$ | |
| 31 | $10 \cdot 10^2$ | |

In a further advantageous variant, during the preparation of the composite materials, instead of the Zn or together with the Zn, additionally Cu(II) complexes can be added. Complexes of this type likewise have a high affinity to sulfur-containing and oxygen-containing compounds and can be added to the composite material 11 for example to optimize the absorption effect on certain contaminants 5.1, 5.2. Other metals, such as, for example Hg, Sn, Fe or Pb, in neutral or ionic form, or bonded in a chemical compound, can also be admixed as biocide active ingredients and/or absorbers.

For uses under chemically aggressive and/or mechanically demanding conditions, such as e.g. at high pressure in fluid 6, instead of or together with the organic components (acrylamide, alginates, amines or polysaccharides) it is also possible to use other substances which form or have porous structures as substrate materials for the solid biocides 1 or the composite materials 11. In particular inorganic compounds, such as e.g. zeolites, are suitable.

Instead of an encapsulation, both the solid biocides (examples A and B) and also the composite materials (examples C and D) can be cast in the form of plates, cuboids, polyhedra or other forms, which are appropriate e.g. for use in a fluid tank or reservoir. In particular, the solid biocides which have a long-lasting effect can also be applied as coating to the vessel walls of the container with the fluid 6 to be purified.

Solid biocides 1 or composite materials 11 in the form of particles or as granulate can also be integrated into an inactive and for the fluid 6 permeable carrier material, a housing or a cage-like structure so that the individual particles or grains do not swim around loose in the fluid.

Alternatively to the described procedure, the solid biocides 1 can also be added to the fluid 6 to be purified at the same time as the composite materials for the absorption and active ingredient release 11. This is possible because the purifying and sterilizing effect of the composite materials 11 starts very rapidly and the contamination of the solid biocides 1 by the contaminants is a much slower process. Thus, it is evident from FIG. 4 that sulfur compounds in an emulsion of the type 7788 are completely removed by the composite material 11 after just 30 min. Likewise, most of the investigated emulsions for the same concentration of composite material 11 are free from bacteria after just 24 h (see in this regard table 2). As is evident form table 3, the solid biocides 1 tolerate in the short term, i.e. for a few days, also bacteria concentrations of up to $50 \cdot 10^3$ bacteria/ml without losing their surface activity and biocidal effect at the same time.

Instead of the described emulsions, it is also possible to treat other fluid 6 with the process according to the invention. In particular, it was found that aqueous solutions which have been admixed with *Escherichia coli* bacteria (abbreviated to *E. coli*) can be sterilized and preserved. *E. coli*, which can multiply in aqueous physiological fluids, lead in humans outside of the intestinal region to a series of serious infections, such as e.g. urinary tract infections, peritonitis (following operations in the abdominal cavity), or meningitis in newborns (infection during birth). Specifically, *E. coli* bacteria were cultivated in a Petri dish and diluted with filtered Evian™ water to a concentration of 106 cells per milliliter. Solid biocide 1 was then added to a solution of this type with a concentration of 99 mg/l. After an incubation time of 72 h, the concentration of the bacteria was determined by the process described above. Here, it was no longer possible to detect *E. coli*. These results show that the process according to the invention is also suitable for applications in the medical sector or in the sanitary sector for the purification of drinking water or bathing water.

In summary, it is found that a new process and a combination preparation has been developed for the sterilization and long-term preservation of fluids. The process is based on the combination of an absorbing and active ingredient-releasing composite material 11 with a catalytically effective solid biocide 1. On account of the effect of composite material 11, the contamination of the surface-active solid biocide 1 is prevented, only as a result of which a long-term effect is facilitated. By virtue of the products according to the invention and the process, it is possible in particular to minimize the required amounts of sterilizing agent and preservative.

The invention claimed is:

1. A product, comprising a mixture of a solid biocide granulate and a composite material in granulate form, which composite material comprises a hydrogel substrate and incorporates and/or has bonded therein a silver (Ag) complex as an active ingredient, as a combination preparation for the simultaneous application during a sterilization and long-term preservation of a fluid to be purified,
    wherein said composite material is configured such that it absorbs contaminants from the fluid and comprises a substrate and incorporated and/or bonded metal compounds as active ingredients, wherein said solid biocide is selected such that, upon adding a solid biocide to the fluid, no metal compounds are released into the fluid,
    wherein said solid biocide granulate and said composite material granulate are added to the fluid, and
    wherein said composite material releases active ingredients which reduce the contaminants and/or sterilize the fluid.

2. The product as claimed in claim 1, characterized in that the solid biocide is configured such that, upon contact, with microorganisms, it produces a germicidal effect on the microorganisms on account of a catalytic mechanism.

3. The product as claimed in claim 1, characterized in that the fluid to be purified with the product is in the form of an emulsion.

4. The product as claimed in claim 1, characterized in that the composite material for the absorption of contaminants and release of active ingredients is configured so that it absorbs and/or precipitates out sulfur and/or organic and/or inorganic sulfur compounds which are present as contaminants in the fluid and/or converts them chemically into an inert form.

5. The product as claimed in claim 1, characterized in that the active ingredients released from the composite material have an antibiotic effect, which is a bactericidal and/or fungicidal effect, and that the released active ingredients lead to a precipitation of the contaminants in the fluid as solids and/or convert the contaminants into an inert form by a chemical reaction.

6. The product as claimed in claim 1, characterized in that the active ingredients released by the composite material are additionally metals or metal compounds of Cu and/or Zn.

7. The product as claimed in claim 1, characterized in that the solid biocide comprises a substrate and metal compounds which are arranged on and/or bonded to the surface of the substrate.

8. The product as claimed in claim 7, characterized in that the substrate of the solid biocide comprises alginates and additionally comprises polyacrylamides and/or amines and/or aluminum silicates or zeolites.

9. The product as claimed in claim 7, characterized in that silver in the metal compounds that are arranged on and/or bonded to the surface of the substrate of the solid biocide is present as a silver amino complex.

10. The product as claimed in claim 7, characterized in that the substrate of the solid biocide is configured as a hydrogel that is swellable and/or elastic.

11. The product as claimed in claim 1, characterized in that the individual grains of the granulates of said solid biocide and said composite material have a diameter of 0.1-5 mm.

12. A process for purifying a fluid using a product as claimed in claim 1, characterized in that the fluid to be purified
    is treated with the composite material for absorption and release of active ingredients, and with the surface-active solid biocide,
    whereby the solid biocide and composite material are added simultaneously to the fluid to be purified.

13. The product as claimed in claim 1, characterized in that the hydrogel is swellable and/or elastic.

14. The product as claimed in claim 1, characterized in that the Ag complex is an Ag amino complex.

15. The product as claimed in claim 1, characterized in that the individual grains of the granulates of said solid biocide and said composite material have a diameter of 0.5-1.2 mm.

* * * * *